United States Patent [19]
Finch et al.

[11] 3,988,334
[45] Oct. 26, 1976

[54] METHOD FOR METHANATION

[75] Inventors: Jack N. Finch; Dennis L. Ripley, both of Bartlesville, Okla.

[73] Assignee: Phillips Petroleum Company, Bartlesville, Okla.

[22] Filed: May 16, 1975

[21] Appl. No.: 578,056

[52] U.S. Cl................. 260/449.6; 48/197 FM; 252/466 B; 252/465; 252/458; 252/460
[51] Int. Cl.$^2$............................................ C07C 1/04
[58] Field of Search................ 260/449.6 M, 449 M; 48/197

[56] References Cited
UNITED STATES PATENTS

| | | | |
|---|---|---|---|
| 2,911,357 | 11/1959 | Myers | 208/138 |
| 3,267,025 | 8/1966 | Gring et al. | 208/136 |
| 3,271,326 | 9/1965 | Forney | 260/449 R |
| 3,334,055 | 8/1967 | Dowden et al. | 252/473 |
| 3,730,694 | 5/1973 | Wunderlich | 260/449 M |
| 3,787,468 | 1/1974 | Fleming et al. | 260/449 M |
| 3,854,895 | 12/1974 | Muller | 260/449 M X |
| 3,901,667 | 8/1975 | Herrmann | 260/449 M |
| 3,904,386 | 9/1975 | Graboski | 260/449 M |

*Primary Examiner*—Howard T. Mars

[57] ABSTRACT

A method is provided for producing methane in which hydrogen and carbon monoxide are contacted in the presence of a supported nickel or cobalt catalyst which is further promoted by a noble metal of Group VIII of the Periodic Table. In an embodiment of the invention a metal from Group VIB of the Periodic Table, preferably tungsten, is used along with the Group VIII noble metal to promote the methanation reaction.

4 Claims, No Drawings

3,988,334

METHOD FOR METHANATION

BACKGROUND OF THE INVENTION

This invention relates to the production of methane. In one of its aspects this invention relates to an improved catalyst system for the production of methane. In yet another of its aspects this invention relates to a process for producing methane using a catalyst less susceptible to sulfur poisoning than those systems currently in use.

It is currently becoming more of interest to produce synthesis gases suitable for use as fuel gas for both home and industry. In the production of synthesis gas, for example, by the steam reforming of hydrocarbon and coal char and by blending hydrogen and carbon monoxide, it it often advantageous to mix methane into the synthesis gases to enrich the fuel content of the gases. It has, therefore, become important to find improved processes for the production of methane by synthesis from carbon monoxide and hydrogen.

One of the problems encountered in the synthesis of methane from carbon monoxide and hydrogen is the presence of sulfur in many available feed streams for the processes. The development of methanation catalysts that are less susceptible to sulfur poisoning than catalysts in current use can provide an overall increase in the production of methane during a given period of reaction.

It is therefore an object of this invention to provide a method for synthesizing methane from carbon monoxide and hydrogen using a catalyst system of improved effectiveness and less susceptible to sulfur poisoning than the catalyst presently in use.

Other aspects, objects and the various advantages of this invention will become apparent upon reading this specification and the appended claims.

SUMMARY OF THE INVENTION

In accordance with the present invention a method is provided for producing methane which comprises contacting hydrogen with carbon monoxide in the presence of a supported catalyst chosen from nickel or cobalt with the reaction further promoted by a noble metal of Group VIII of the Periodic Table. Optionally, a metal from Group VIB of the Periodic Table can be used in conjunction with the Group VIII noble metal as promoter of the methanation reaction.

In this invention the reaction process produces methane by the low temperature methanation of a synthesis gas generally described as consisting of three volumes of hydrogen with one volume of carbon monoxide. Although a stoichiometric ratio of hydrogen to carbon monoxide of about 3 is utilized in the reaction, deviation from this ratio can be tolerated and is expected. Generally, it is preferred that a stoichiometric ratio of about 2.8 to about 3.2 be used. The methane that is produced is recovered from the reaction mixture and can be used as a constituent of synthetic natural gas or for any other desired purpose. Synthesis gas can be made conventionally by steam reforming of hydrocarbon and coal char and by blending hydrogen and carbon monoxide obtained from suitable refinery streams.

The catalysts of this invention are nickel or cobalt on a suitable support such as alumina, silica, zirconia, silica-alumina, or other combinations of support material. The catalysts are promoted by a noble metal of Periodic Group VIII and optionally a Group VIB metal such as chromium, molybdenum, or tungsten in addition to the Group VIII noble metal. A presently preferred Group VIB metal is tungsten. A presently preferred support is catalytic grade alumina.

The supported noble metal promoters alone are not effective at the low metal concentrations and the low reaction temperatures employed in converting the synthesis gas to methane. However, the noble metal promoters enhance the activity of the nickel and cobalt supported catalysts to increase the conversion to methane. In addition, the noble metal promoted catalysts maintain greater activity for methane conversion than the unpromoted catalysts in the presence of a sulfur poison such as carbon disulfide. Even though the quantity of carbon disulfide required completely to deactivate the promoted or unpromoted catalysts is about the same, the resistance to sulfur poisoning exhibited by the noble metal promoted catalysts enables more methane to be produced overall by these catalysts than by the unpromoted catalysts. The promoted catalysts can, therefore, be advantageously employed with synthesis gas containing low sulfur concentrations when necessary.

The noble metals contemplated as promoters in this invention include all the six platinum group metals, i.e., ruthenium, rhodium, palladium, osmium, iridium and platinum. The concentration of promoter metal can vary from about 0.05 to 5 wt. percent of the weight of the total catalyst composite although for purposes of economy a range of about 0.1 to about 1 wt. percent is presently preferred. Total catalyst composite for this invention means catalyst, promoter metal, and support.

The cobalt and nickel concentrations used in the supported catalyst compositions generally range from about 5 to about 20 wt. percent of total catalyst composite with about 5 to about 15 wt. percent presently preferred.

The concentration of Group VIB metal such as tungsten in the catalysts can range from about 10 to about 60 wt. percent of total catalyst composite. Good results have been obtained with about 20 to about 50 wt. percent.

The reaction temperatures employed in the practice of this invention can vary over a wide range but will most generally fall within a practical range from about 200° to about 450° C, more preferably from about 275° to about 350° C. The pressures employed can also vary over a wide range but will generally fall within the range from about 0 to about 12,000 psig. The gaseous hourly space velocity (GHSV) in terms of volumes of gas per volume of catalyst per hour can range from about 200 to about 10,000. Particularly good results have been obtained at about 600 to about 5000 GHSV.

All the runs presented in the following examples were conducted in a continuous flow reactor operating at atmospheric pressure. Reactor effluents were analyzed by gas-liquid chromatography. Generally, carbon monoxide was continuously injected at about 13 cc/minute STP into hydrogen flowing at about 39 cc/minute STP to give synthesis gas in about stoichiometric proportions, i.e., $H_2/CO_3$ volume ratio of 3 or near 3. The catalysts were in the form of 16–60 mesh particles. To minimize temperature effects in the catalyst bed the catalysts were generally diluted with 5 times their weight of 16–60 mesh alumina particles. This practice was not followed with the catalysts containing tungsten since the concentration of the nickel was approximately the same as in the diluted catalysts.

Presentation of conversion data poses problems because widely different $CH_4$ yields are possible for a given CO conversion. Since the $H_2/CO$ ratios are generally about 3 a formula proposed by the Institute of Gas Technology was used to express the percent $H_2$—CO conversion. This parameter which expresses conversion of $H_2$ and CO to $CH_4$ on an equal basis is defined in simplified form as follows:

$$100 \left[ 4 \frac{(\text{moles dry product gas})}{(\text{moles dry feed})} - \text{mole fraction } CH_4 \text{ in dry product gas} \right]$$

EXAMPLE 1

Catalyst A, consisting of alumina containing platinum, was prepared by impregnation of alumina with an aqueous solution of platinum diamminodinitrite, $Pt(NO_2)_2(NH_3)_2$, sufficient to give 0.15 wt. percent platinum based on the calcined composite. The resulting mixture was dried at 125° C in air and calcined in air for 1 hour at 500° C.

Catalyst B, consisting of alumina containing 10 wt. percent cobalt based on the calcined composite, was prepared by impregnating alumina with sufficient aqueous cobaltous nitrate solution to give the desired cobalt content. The resulting mixture was dried at 125° C and calcined in air at 500° C for 1 hour.

Catalyst C, consisting of alumina containing 10 wt. percent cobalt and 0.15 wt. percent platinum based on the calcined composite was prepared by impregnating a portion of the wet composite of catalyts B with an aqueous solution of platinum diamminodinitrite sufficient to give the desired platinum content. The resulting mixture was dried at 125° C and calcined in air at 500° C for 1 hour.

Each catalyst was individually charged to the reactor, heated to 500° C under flowing hydrogen for 2 hours, then cooled to 300° C under hydrogen and the run was begun by charging the synthesis gas to the reactor. The reaction conditions employed including addition of $CS_2$ to the gas and the results obtained are presented in Table I. The $H_2/CO$ ratios shown are volume ratios. When used, $CS_2$ was injected into the synthesis gas feed above the catalyst bed.

Inspection of the data presented in Table I reveals that in run 1 the $Pt.Al_2O_3$ catalyst is not active for production of methane from synthesis gas at 300° C. It has fairly good activity at 550° C since 24 percent conversion was obtained, but the activity dropped sharply to near zero with the addition of the $CS_2$ poison. The run 2 data show that the $Co.Al_2O_3$ catalyst is effective for conversion of synthesis gas to $CH_4$ at 300° C. The addition of $CS_2$, however, completely poisoned the catalyst. There was no evidence of recovery of catalytic activity even at 450° C. This effect was expected. The run 3 results unexpectedly show that a small quantity of platinum on the cobalt catalyst of run 2 substantially increases the activity of the catalyst as evidenced by the increase in conversion after 0.5 hour from 52.9 percent (control) to 75.2 percent. After catalyst C was poisoned by the addition of $CS_2$ to the feed it was found that the catalyst activity was slowly regained as the reaction temperature was increased from 350° C to 550° C.

Table I

The Methanation Activity of Platinum, Cobalt and Platinum-Cobalt Catalysts

| Run | Catalyst, metal, wt. % | time on Stream hrs | Conversion to $CH_4$, % | Temp. °C | $O_2$ | $N_2$ | $H_2$ | CO | $CO_2$ | $C_1$ | $C_2$ | $C_3$ | $C_3^=$ | $n,C_4$ |
|---|---|---|---|---|---|---|---|---|---|---|---|---|---|---|
| 1 Control | Pt-0.15 | 0.5 | 0 | 300 | .06 | .35 | 72.0 | 27.5 | 0 | 0 | 0 | 0 | 0 | 0 |
|  | Pt-0.15 | 2.0 | 0 | 300 | .09 | .30 | 70.0 | 29.6 | 0 | 0 | 0 | 0 | 0 | 0 |
|  | Pt-0.15 | 2.5 | 0.64 | 350 | .12 | .36 | 69.5 | 29.8 | .05 | .16 | 0 | 0 | 0 | 0 |
|  | Pt-0.15 | 4.5 | 24.0 | 550 | .10 | .26 | 65.9 | 26.3 | 3.3 | 6.9 | 0 | 0 | 0 | 0 |
|  | Pt-0.15 | 5.0 | 1.4 | 550 | .14 | .42 | 72.7 | 26.2 | .19 | .36 | 0 | 0 | 0 | 0 |
| 2 Control | Co-10 | 0.5 | 52.9 | 300 | .08 | .29 | 56.7 | 19.9 | 1.9 | 20.6 | .41 | .03 | 0 | 0 |
|  | Co-10 | 1.65 | 0 | 300 | .08 | .24 | 70.1 | 29.5 | .03 | 0 | 0 | 0 | 0 | 0 |
|  | Co-10 | 3.35 | 0 | 450 | .12 | .37 | 69.7 | 29.5 | .17 | 0 | 0 | 0 | 0 | 0 |
| 3 Invention | Co-10 Pt-0.15 | 0.5 | 75.2 | 300 | .12 | .45 | 46.3 | 4.2 | 10.8 | 37.5 | 0.57 | .04 | 0 | .02 |
|  | Co-10 Pt-0.15 | 1.5 | 0 | 350 | .09 | .29 | 69.2 | 30.3 | .10 | 0 | 0 | 0 | 0 | 0 |
|  | Co-10 Pt-0.15 | 3.0 | 0.24 | 500 | .11 | .34 | 69.6 | 29.6 | .27 | .06 | 0 | 0 | 0 | 0 |
|  | Co-10 Pt-0.15 | 3.5 | 0.98 | 550 | .08 | .25 | 69.2 | 29.6 | .44 | .25 | .09 | 0 | .02 | 0 |
|  | Co-10 Pt-0.15 | 4.5 | 2.5 | 550 | .17 | .56 | 71.1 | 26.5 | .79 | .64 | .19 | 0 | .03 | 0 |

| Run | Space Velocity v/v/r | Remarks |
|---|---|---|
| 1 Control | 4480 | $H_2/CO = 3.0$, 0.351 g cat. used |
|  | 4480 |  |
|  | 4480 |  |
|  | 4480 |  |
|  | 4480 | added 10 µl $CS_2$ just after 4.5 hrs, activity decreases |
| 2 Control | 4450 | $H_2/CO = 2.95$, 0.35 g cat. used |
|  | 4450 | added 10 µl $CS_2$, just after 0.5 hrs, activity ceases |
|  | 4450 | no evidence of recovery of catalytic activity ~2 |

Table I-continued

The Methanation Activity of Platinum, Cobalt and Platinum-Cobalt Catalysts

|   |   | 4450 | atoms Co to 1 atom S $H_2/CO = 2.99$, 0.35 g Cat. used |
|---|---|---|---|
| 3 | Invention | 4450 | added 10 μl $CS_2$ just after 0.5 hrs (~2 atoms Co to 1 of S) activity ceases |
|   |   | 4450 | catalyst activity slightly recovering |
|   |   | 4450 | catalyst activity slightly recovering |
|   |   | 4450 | catalyst activity slightly recovering |

EXAMPLE II

Another series of cobalt and nickel catalysts was prepared some of which were additionally promoted by a platinum group metal or tungsten and tungsten plus platinum. The effect of incremental poisoning of the catalyst with small amounts of $CS_2$ added to the feed was studied. Unless otherwise noted, each catalyst was prepared by impregnating the alumina support with an aqueous solution of a cobalt salt or a nickel salt and/or with an aqueous solution of a platinum group metal sufficient to give the desired quantity of promoter or promoters based on the calcined composite. Each mixture was dried and calcined as described in Example I. The nickel-tungsten-alumina catalyst was obtained commercially. A portion of this catalyst was impregnated with an aqueous solution of platinum diamminodinitrite sufficient to obtain the desired quantity of platinum. Each catalyst was individually charged to the reactor and treated with flowing hydrogen in the manner described in Example I before each run was started. All runs were conducted at 300° C and at atmospheric pressure. The $CS_2$ was added incrementally in 1, 2 or 2.5 microliter quantities to the feed. The results are presented in Table II.

Inspection of the results shows that the control catalysts in the absence of $CS_2$ range from poor to good in converting synthesis gas to methane after on stream 30 minutes. That is, the ruthenium-alumina catalyst (run 9) showed a conversion of 2.5 percent, the cobalt-alumina catalyst (run 4) showed a conversion of 49 percent and the nickel-alumina catalyst (run 6) showed a conversion of 87.2 percent. The tungsten promoted nickel-alumina catalyst (run 11) shows rather poor activity also since a conversion of only 13 percent was obtained after 30 minutes on stream.

Table II

The Effect of Sulfur Poisoning on the Methanation Activity of Promoted Nickel and Cobalt Catalysts

| Run | 4 Control Co, 10 wt. % | | | | | 5 Invention Co, 10 wt. % Pt, 0.15 wt. % | | | | | 6 Control Ni, 10 wt. % | | | | |
|---|---|---|---|---|---|---|---|---|---|---|---|---|---|---|---|
| Time Hrs. | $H_2/CO$ | 0.357 g GHSV | Con. | $CS_2$ | Atom Ratio Co/S | $H_2/CO$ | 0.35 g GHSV | Con. | $CS_2$ | Atom Ratio Co/S | $H_2CO$ | 0.35 g GHSV | Con. | $CS_2$ | Atom Ratio Ni/S |
| 0.5 | 3.0 | 4355 | 49.0 | 0 | — | 3.0 | 4428 | 69.8 | 0 | — | 2.9 | 4310 | 87.2 | 0 | — |
| 1.0 | 3.0 | 4355 | — | — | — | 3.0 | 4428 | — | — | — | 2.9 | 4310 | — | — | — |
| 1.5 | 3.0 | 4355 | — | — | — | 3.0 | 4428 | — | — | — | 2.9 | 4310 | — | — | — |
| 2.0 | 3.0 | 4355 | 21.5 | 2 | 9 | 3.0 | 4428 | 44.5 | 2 | 9 | 2.9 | 4310 | 76.8 | 1 | 18 |
| 2.5 | 3.0 | 4355 | 11.9 | 4 | 4.6 | 3.0 | 4428 | 21.7 | 4 | 4.6 | 2.9 | 4310 | 79.5 | 2 | 9 |
| 3.0 | 3.0 | 4355 | — | — | — | 3.0 | 4428 | — | — | — | 2.9 | 4310 | 76.6 | 3 | 6 |
| 3.5 | 3.0 | 4355 | 0 | 6 | 3 | 3.0 | 4428 | .56 | 6 | 3 | 2.9 | 4310 | 60.9 | 4 | 4.6 |
| 4.0 | 3.0 | 4355 | 0 | 8 | 23 | 3.0 | 4428 | 0 | 8 | 23 | 2.9 | 4310 | 51.2 | 5 | 3.8 |
| 4.5 | 3.0 | 4355 | 0 | 10 | 2 | 3.0 | 4428 | 0 | 10 | 2 | 2.9 | 4310 | 36.7 | 6 | 3 |
| 5.0 | | | | | | | | | | | 2.9 | 4310 | 21.9 | 7 | 2.6 |
| 5.5 | | | | | | | | | | | 2.9 | 4310 | 10.0 | 8 | 2.3 |
| 7.5 | | | | | | | | | | | | | | | |

| Run | 7 Invention Ni, 10 wt. % Pt, 0.15 wt. % | | | | | 8 Invention Ni, 10 wt. % Pd, 0.15 wt. % | | | | | 9 Ru, 0.5 wt. % | | | | |
|---|---|---|---|---|---|---|---|---|---|---|---|---|---|---|---|
| Time Hrs. | $H_2/CO$ | 0.35 g GHSV | Con. | $CS_2$ | Atom Ratio Ni/S | $H_2/CO$ | 0.331 g GHSV | Con. | $CS_2$ | Atom Ratio Ni/S | $H_2/CO$ | 0.35 g GHSV | Con. | $CS_2$ | Atom Ratio Ru/S |
| 0.5 | 2.9 | 4343 | 85.5 | 0 | — | | | ~87 | 0 | — | 3.2 | 4538 | 2.5 | 0 | — |
| 1.0 | 2.9 | 4343 | — | — | — | | | — | | | | | | | |
| 1.5 | 2.9 | 4343 | — | — | — | | | — | | | 3.2 | 4538 | 3.2 | 0 | — |
| 2.0 | 2.9 | 4343 | 84.8 | 1 | 18 | | | 86.5 | 1 | 15 | 3.2 | 4538 | 3.0 | 1 | .6 |
| 2.5 | 2.9 | 4343 | 82.5 | 2 | 9 | | | 83.8 | 2 | 9 | 3.2 | 4538 | 2.9 | 2 | .3 |
| 3.0 | 2.9 | 4343 | 80.5 | 3 | 6 | | | 88.4 | 3 | 6 | 3.2 | 4538 | 2.6 | 3 | .2 |
| 3.5 | 2.9 | 4343 | 78.3 | 4 | 4.6 | | | 82.0 | 4 | 4.6 | 3.2 | 4538 | 2.6 | 4 | .15 |
| 4.0 | 2.9 | 4343 | 79.0 | 5 | 3.8 | | | 82.9 | 5 | 3.8 | | | | | |
| 4.5 | 2.9 | 4343 | 78.9 | 6 | 3 | | | 71.9 | 6 | 3 | | | | | |
| 5.0 | 2.9 | 4343 | 70.2 | 7 | 2.6 | | | 8.5 | 7 | 2.6 | | | | | |
| 5.5 | 2.9 | 4343 | 25.7 | 8 | 2.3 | | | 1.0 | 8 | 2.3 | | | | | |
| 7.5 | | | | | | | | | | | | | | | |

| Run | 10 Invention Ni, 10 wt. % | 11 Control Ni, 5.4 wt. % | 12 Invention Ni, 5.4 wt. % |
|---|---|---|---|

Table II-continued

The Effect of Sulfur Poisoning on the Methanation Activity of Promoted Nickel and Cobalt Catalysts

| | Ru, 0.5 wt. % | | | | | W, 21.3 wt. % | | | | | Pt, 0.15 wt. % W, 21.3 wt. % | | | | |
|---|---|---|---|---|---|---|---|---|---|---|---|---|---|---|---|
| Time Hrs. | H₂/CO | 0.35 g GHSV | Con. | CS₂ | Atom Ratio Ni/S | H₂/CO | 2.0 g GHSV | Con. | CS₂ | Atom Ratio Ni/S | H₂/CO | 2.0 g GHSV | Con. | CS₂ | Atom Ratio Ni/S |
| 0.5 | 3.0 | 4535 | 88.6 | 0 | — | 2.9 | 950 | 13.0 | 0 | — | 3.0 | 966 | 89.8 | 0 | — |
| 1.0 | | | | | | 2.9 | 950 | 9.6 | 2.5 | 22 | 3.0 | 966 | 84.0 | 2.5 | 22 |
| 1.5 | 3.0 | 4535 | 86.0 | 0 | — | 2.9 | 950 | 7.2 | 5.0 | 11 | 3.0 | 966 | 84.2 | 5.0 | 11 |
| 2.0 | 3.0 | 4535 | 79.7 | 2 | 9 | 2.9 | 950 | 5.2 | 7.5 | 7.2 | 3.0 | 966 | 84.2 | 7.5 | 7.2 |
| 2.5 | 3.0 | 4535 | 82.2 | 4 | 4.6 | 2.9 | 950 | 3.6 | 10 | 5.4 | 3.0 | 966 | 84.2 | 10.0 | 5.4 |
| 3.0 | 3.0 | 4535 | 79.4 | 6 | 3 | 2.9 | 950 | 2.3 | 12.5 | 4.4 | 3.0 | 966 | — | 12.5 | 4.4 |
| 3.5 | 3.0 | 4535 | 2.4 | 8 | 2.3 | 2.9 | 950 | 1.2 | 15 | 3.6 | 3.0 | 966 | 83.7 | 17.5 | 3.1 |
| 4.0 | 3.0 | 4535 | .35 | 10 | 2 | | | | | | 3.0 | 966 | 84.2 | 17.5 | 3.1 |
| 4.5 | | | | | | | | | | | 3.0 | 966 | — | — | — |
| 5.0 | | | | | | | | | | | 3.0 | 966 | 1.9 | 17.5 | 2 |
| 5.5 | | | | | | | | | | | 3.0 | 966 | .4 | 32.5 | 1.6 |
| 7.5 | | | | | | | | | | | | | | | |

Notes:
H₂/CO is volume ratio
Con. = conversion of H₂CO to CH₄, %
GHSV = gaseous hourly space velocity, volumes gas/volume catalyst/hour
CS₂ = total volume of CS₂ in μl added by syringe to feed Each of the previous catalysts show a steadily decreasing activity as carbon disulfide is added incrementally to the feed. However, when the control catalysts of runs 4, 6 and 11 are additionally promoted with a platinum group metal such as platinum, palladium and ruthenium it can be seen, particularly with the nickel-containing catalysts, that considerable resistance to sulfur poisoning is imparted. Compare runs 4, 5, and run 6 with runs 7, 8, and 10, and run 11 with run 12. The platinum group promoters enables the catalysts to maintain good activity until the critical concentration of poison is reached. Therefore, these catalysts produce more methane than do the corresponding control catalysts. Also, it is to be noted that the nickel-tungsten-platinum catalyst is substantially more active as well as sulfur resistant than the catalyst in the absence of platinum. The sulfur resistance of the catalysts promoted by platinum group metals is perhaps more clearly shown by comparing the atom ratio of cobalt or nickel to sulfur with conversion of the feed containing measured amounts of CS₂ to methane. For example, in the control catalyst of run 6, when the Ni/S ratio equals 3, the conversion has dropped from the initial 87.2 percent to 36.7 percent. With invention catalyst of run 7 when the Ni/S ratio equals 3, the conversion has dropped from the initial 85.5 percent to only 78.9 percent which represents only a slight decline.

We claim:

1. A method for producing methane comprising contacting hydrogen and carbon monoxide within a temperature range of about 200° C to about 450° C in the presence of a supported catalyst composite comprising a metal chosen from nickel and cobalt in an amount in the range of about 5 to about 20 weight percent of the catalyst composite; with the catalyst further promoted by a noble metal of Group VIII of the Periodic Table in an amount in the range of about 0.05 to about 5 weight percent of the catalyst composite; and a Group VIB metal in an amount in the range of from about 10 to about 60 weight percent of the catalyst composite.

2. A method of claim 1 wherein the catalytic support is chosen from among alumina, silica, zirconia, silica-alumina, and mixtures thereof; the noble metals are chosen from ruthenium, rhodium, palladium, osmium, iridium, and platinum; and the Group VIB metal is chosen from among chromium, molybdenum, and tungsten.

3. The method of claim 2 wherein the ratio of hydrogen to carbon monoxide used in the reaction is in the range of about 2.8 to about 3.2.

4. The method of claim 3 wherein the Group VIB metal is tungsten.

* * * * *